United States Patent [19]

Iwahashi

[11] Patent Number: 5,360,574
[45] Date of Patent: Nov. 1, 1994

[54] GEL-FORM DEODORANT COMPOSITION CONTAINING CHLORIDE DIOXIDE

[75] Inventor: Takashi Iwahashi, Sagamihara, Japan

[73] Assignee: Aikoh Co., Ltd., Japan

[21] Appl. No.: 867,228

[22] PCT Filed: Dec. 4, 1989

[86] PCT No.: PCT/JP89/01215
§ 371 Date: Jun. 2, 1993
§ 102(e) Date: Jun. 2, 1993

[87] PCT Pub. No.: WO91/07995
PCT Pub. Date: Jun. 13, 1991

[51] Int. Cl.$^5$ .............................................. A61L 9/01
[52] U.S. Cl. ............................. 252/187.21; 424/76.1; 424/76.2; 424/76.3; 424/76.4; 424/76.7
[58] Field of Search ................... 424/76.1, 76.2, 76.3, 424/76.4, 76.7; 252/187.21

[56] References Cited

FOREIGN PATENT DOCUMENTS

| 0277398 | 8/1988 | European Pat. Off. . |
| 50-26784 | 3/1975 | Japan . |
| 57-22102 | 2/1982 | Japan . |
| 62-19171 | 1/1987 | Japan . |
| 2172891 | 10/1986 | United Kingdom . |

*Primary Examiner*—José G. Dees
*Assistant Examiner*—Dwayne C. Jones
*Attorney, Agent, or Firm*—Larson and Taylor

[57] ABSTRACT

This invention provides a deodorant composition in the form of gel containing chlorine dioxide, which comprises a gel product obtained by gelling an aqueous solution of stabilized chlorine dioxide with the use of both a polyethylene-imide having a molecular weight of from 10,000 to 100,000 and an epoxide crosslinking agent. The gel typed deodorant composition according to this invention is effective for deodorizing sulfur-containing compounds, has a high strength because of its solid gel form and a long-term stability, and is easy to handle including the time of exchanging the deodorant composition for another one.

2 Claims, No Drawings

GEL-FORM DEODORANT COMPOSITION CONTAINING CHLORIDE DIOXIDE

TECHNICAL FIELD OF THE INVENTION

This invention relates in its purpose to the gelation of a stabilized chlorine dioxide which has an excellent oxidizing capacity against sources of generating malodors in wide-spread fields ranging from the industrial world to domestic houses, particularly against acidic odor-generating substances namely sulfur-containing compounds such as hydrogen sulfide and mercaptan and which are useful to make the sources odorless entirely. When converted the stabilized chlorine dioxide by the gelation into the form of gel, the resultant gel has some advantages that it has a good handlability when used as a deodorizer namely deodorant composition and that the time of exchanging the deodorant composition for new one can be determined with naked eyes, because the gel per se becomes reduced in volume or in size with the lapse of time.

BACKGROUND OF THE INVENTION

There are many already known processes for the deodorization of malodors, which may mainly be classified into the four species mentioned below.

(i) A physical method by the use of an adsorber for example active carbon (adsorption mechanism).

(ii) A method which relies on chemical reactions such as oxidation and neutralization by the use of chemical substances.

(iii) A biological method by the use of microorganism.

(iv) A masking method by the use of fragrant.

The deodorization mechanism of chlorine dioxide is believed to be an oxidizing reaction which corresponds to the above-mentioned method (ii). Since the presence of chlorine dioxide was published in 1802 by R. Chenvix, actual preparation of chlorine dioxide was made in 1851 to 1816. Chlorine dioxide is a very explosive and corrosive compound and it was difficult to store and transport the former. When used actually, hence, chlorine dioxide has been produced directly by the user. Chlorine dioxide was, however, focused on its excellent properties such as oxidizing, bleaching and antibacterial activities and so extensive studies were developed in an attempt to seek for a product which is possible to handle easily to everyone. As a result of such studies, there was prepared a compound called stabilized chlorine dioxide into which a stabilizing agent such as alkali or alkaline earth compound is incorporated. The aqueous stabilized chlorine dioxide solution was being adjusted to a pH of 7.5 to 10.0 and made acidic or neutral by the addition of an acidic substance when used thereof. In particular, it is believed that the antibacterial activity of stabilized chlorine dioxide is better at an acidic range than that at an alkaline range. Now, general considerations on the effect and activity of stabilized chlorine dioxide are disclosed in several articles (please refer to J. Odor Research and Eng. vol. 19, pages 328 to 331 (1988); vol. 20, pages 81 to 85 (1989)). The commercially available aqueous stabilized chlorine dioxide solution has a concentration of about 50,000 ppm (approximately 5%) at its maximum, which was employed as such according to this invention.

The stabilized chlorine dioxide has been mainly used in the form of liquid and in other cases there was also known a solid stabilized chlorine dioxide in which the stabilized chlorine dioxide solution was adsorbed on and impregnated into a solid carrier such as zeolite, silica gel, calcium silicate and the like (please refer to Japanese Patent KOKAI No. 63-147468). In case of the aqueous stabilized chlorine dioxide solution, it must be used as such by conventional means e.g. spraying against malodors and so it becomes difficult to use the liquid chlorine dioxide at standard households since it exerts strongly an irritating chlorine smell. In case of the solid stabilized chlorine dioxide adsorbed on and impregnated into zeolite and the like, further, it has been used for the deodorization of refrigerators, but it was difficult to determine a decreased deodorizing activity thereof. As contrary to the liquid stabilized chlorine dioxide, besides, the solid one has a disadvantage of it being of insufficient preservation i.e. stability properties.

In view of the prior art teaching of Japanese Patent Publn. No. 1-38151, for example, it was observed that no storage period of more than one month was possible regarding the stabilized chlorine dioxide in the form of solid which was obtained by adsorbing on and impregnating into a solid carrier such as zeolite and silica gel, following the addition of an acidic substance to the stabilized chlorine dioxide for the activation of the latter. Typical examples of the acidic substance include a solid acid such as alumina and silica-alumina, a mineral acid such as hydrochloric acid and sulfuric acid, and an organic acid such as oxalic acid and citric acid.

We, the present inventors, have made extensive researches in an attempt to dissolve said technical problems, and we have now found that the aqueous stabilized chlorine dioxide solution can be gelled with using both a polyethylene-imine having a molecular weight of from 10,000 to 100,000 and an epoxide crosslinking agent and that there may be obtained a transparent gelled product which has an increased strength, is entirely free of chlorine smell and of long-term stability.

DISCLOSURE OF THE INVENTION

According to an aspect of this invention, therefore there is provided a deodorant composition in the form of gel containing chlorine dioxide, which comprises a gel product obtained by gelling an aqueous solution of stabilized chlorine dioxide with use of a polyethylene-imine having a molecular weight of from 10,000 to 100,000 and of an epoxide crosslinking agent.

THE BEST FORM FOR THE EMBODIMENT OF THE INVENTION

As characteristic properties of an aqueous chlorine dioxide solution, chlorine dioxide is evaporated and spread positively into atmospheric air in case when the solution is maintained at a pH value of from neutral to acidic range, thereby to result in antibacterial and oxidizing activities of chlorine dioxide. Whereas, this solution has a disadvantage of very poor preservation property. Now, an aqueous solution of polyethylene-imine is alkaline i.e. has a pH of about 11 at 5% by weight solution because of the presence of nitrogen atoms within the molecules, and the use of polyethylene-imine solution is therefore very convenient for the storage of the chlorine dioxide solution. The polyethylene-imine used according to this invention has suitably a molecular weight range of from 10,000 to 100,000 and more particularly from 20,000 to 70,000.

Regarding the lower limit for the molecular weight of polyethylene-imine to be used, it is possible to carry out the gelation of the stabilized chlorine dioxide by using a polyethylene-imine having a lower molecular weight of about 1,000 or a little more, but it becomes necessary to use a volume of polyethylene-imine for example in an amount of 30% by weight or above, and there is present a disadvantage that the use of polyethylene-imine having such a lower molecular weight results in brittle gel which is of poor practical use. Whereas, it is possible to conduct the gelation of the stabilized chlorine dioxide by using polyethylene-imine having a molecular weight of about 10,000 in an amount of 20% by weight and thereby the resultant gel can be well used for the deodorization of malodors. With regard to the upper limit, i.e. 100,000, for the molecular weight of polyethylene-imine to be used, the commercially available polyethylene-imine at present time in Japan has a molecular weight of 100,000, which is to be used.

Typical examples of an epoxide compound to be used as crosslinking agent include compounds containing therein two or more epoxide groups such as ethylene glycol diglycidyl ether, polyethylene glycol diglycidyl ether, propylene glycol diglycidyl ether, polypropylene glycol diglycidyl ether, neopentyl glycol diglycidyl ether, trimethylolpropane polyglycidyl ether, polyglycerol polyglycidyl ether, glycerol polyglycidyl ether and diglycerol polyglycidyl ether.

According to the gel-typed deodorant composition of this invention, the polyethylene-imine compound and epoxide compound are to be used in amounts of 1 to 25% by weight and 0.5 to 15% by weight, respectively. In an amount less than the lower limit thereof, the degree of gelation is insufficient, and in an amount higher than the upper limit thereof, the degree of curing is in excess of the desired one and the rate of deodorization reaction becomes slow. In both the cases, therefore, the resultant gel product cannot be used for practical utility.

The deodorant composition in the form of gel according to this invention can be prepared by admixing together 2 to 90% by weight, preferably 2 to 87.5% by weight of aqueous stabilized chlorine dioxide solution, 1 to 25% by weight, preferably 2 to 20% by weight, of polyethylene-imine having a molecular weight of 10,000 to 100,000 and 0.5 to 15% by weight, preferably 1.5 to 10% by weight, of epoxide crosslinking agent, optionally in an aqueous medium, at ambient temperature and under normal pressure in a reaction container made of glass, polyvinyl chloride or stainless steel.

In preparing the gel-form deodorant composition of this invention, the crosslinking reaction, namely gelation reaction between polyethylene-imine and epoxide compound is, as an example, deemed to proceed with as follows. The polyethylene-imine to be used contains $>N$, $>NH$ and $-NH_2$ groups within the molecular backbone thereof. Amongst those groups, $>NH$ and $-NH_2$ groups react with epoxide rings in the epoxide compound to conduct an addition reaction between them as represented by the following reaction formula:

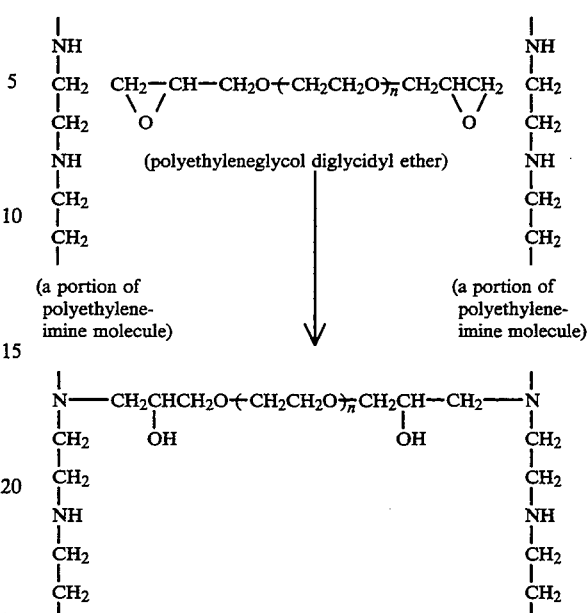

The resulting gel product according to this invention may be used as deodorizer, but the present invention also includes within the range thereof such gel product when used for other utilities, e.g. used for antibacterial purpose.

The present invention is now illustrated by the following Examples which are illustrative of the gelation reaction with using an aqueous stabilized chlorine dioxide solution having a concentration of 50,000 ppm and which demonstrate the deodorization activity of acidic odor with use of the resulting gel typed deodorant composition.

EXAMPLE 1

Each ingredient mentioned below was homogeneously mixed together in a suitable reactor and allowed to stand at ambient temperature (about 25° C.). After the lapse of 30 minutes the gelation proceeded and after about one hour the reaction mixture was completely free of fluidity and produced a desired gel.

| | |
|---|---|
| aqueous stabilized chlorine dioxide solution at 50,000 ppm | 10% by weight |
| polyethylene-imine of molecular weight 70,000 | 2% by weight |
| polyethylenglycol diglycidyl ether of molecular weight 490 | 1.5% by weight |
| water | 86,5% by weight |

EXAMPLE 2

Each ingredient mentioned below was uniformly mixed together and allowed to stand at ambient temperature (about 25° C.). After the lapse of 10 minutes the gelation proceeded and after about 20 minutes the reaction mixture entirely lost its fluidity and produced a desired gel.

| | |
|---|---|
| aqueous stabilized chlorine dioxide solution at 50,000 ppm | 10% by weight |
| polyethylene-imine of molecular | 8% by weight |

-continued

| | |
|---|---|
| weight 70,000 | |
| polyglycerol polyglycidyl ether of molecular weight 742 (3 epoxide groups per molecule) | 3% by weight |
| water | 79% by weight |

EXAMPLE 3

Each component mentioned below was uniformly admixed together and allowed to stand at ambient temperature (about 25° C.). After the lapse of 2 to 3 minutes, the gelation occurred and after about 7 minutes no fluidity was found in the reaction mixture and a desired gel was obtained.

| | |
|---|---|
| aqueous stabilized chlorine dioxide solution at 50,000 ppm | 10% by weight |
| polyethylene-imine of molecular weight 20,000 | 20% by weight |
| polypropylene glycol diglycidyl ether of molecular weight 304 | 10% by weight |
| water | 60% by weight |

EXAMPLE 4

Each ingredient mentioned below was uniformly mixed together and allowed to stand at ambient temperature (about 25° C.). After the lapse of 10 minutes the gelation of the reaction mixture took place and after about 15 minutes no fluidity was found in the reaction mixture and a desired gel product was obtained.

| | |
|---|---|
| aqueous stabilized chlorine dioxide solution at 50,000 ppm | 30% by weight |
| polyethylene-imine of molecular weight 100,000 | 5% by weight |
| polyethylene glycol diglycidyl ether of molecular weight 490 | 2.5% by weight |
| water | 62.5% by weight |

EXAMPLE 5

Each component mentioned below was thoroughly admixed together and allowed to stand at ambient temperature (about 25° C.). After the lapse of 10 minutes, the gelation of the reaction mixture proceeded and after about 20 minutes the reaction mixture lost its fluidity perfectly and there was afforded a desired gel product.

| | |
|---|---|
| aqueous stabilized chlorine dioxide solution at 50,000 ppm | 87.5% by weight |
| polyethylene-imine of molecular weight 100,000 | 10% by weight |
| polyethylene glycol diglycidyl ether of molecular weight 490 | 2.5% by weight |
| water | 0% by weight |

EXAMPLE 6

Each component mentioned below was uniformly mixed together and allowed to stand at ambient temperature (about 25° C.). After the lapse of 10 minutes, the gelation of the reaction mixture occurred and after about 30 minutes, the reaction mixture lost entirely its fluidity and there was obtained a desired gel product.

| | |
|---|---|
| aqueous stabilized chlorine dioxide solution at 50,000 ppm | 2% by weight |
| polyethylene-imine of molecular weight 10,000 | 20% by weight |
| polyethylene glycol diglycidyl ether of molecular weight 490 | 10% by weight |
| water | 68% by weight |

EXAMPLE 7

Now the gel products obtained according to Examples 1 to 6 respectively were used for the deodorization test against acidic malodor gases, methylmercaptan and hydrogen sulfide.

The deodorization test was carried out according to the known head space method and there was used a 500 ml conical flask fitted with a plug at the top thereof, through which two glass tubes having cocks (a) and (b) were passed.

The test procedure employed and the test result obtained were as follows:

(1) Test procedure i) A gel sample (1 g) in a cubic form was hung on a hook located on the plug within the flask. Now the cocks (a) and (b) were being closed.

ii) The cock (a) was opened, the flask subjected to reduced pressure of about 3 mm Hg by a vacuum pump and then the cock (a) closed.

iii) A gas collecting bag, i.e. TEDLAR (polyvinyl fluoride)* bag into which a concentration-adjusted gas (methylmercaptan 45 ppm; hydrogen sulfide 500 ppm) was charged was connected to a gas introduction part upstream of the cock (a) on the plug. The cock (a) was opened to introduce the malodor gas into the flask and then the cock (a) closed and the TEDLAR (polyvinyl fluoride) bag removed from the introduction part. TEDLAR is a trademark for a trade name of polyvinyl fluoride.

iv) After the lapse of predetermined period, the cock (b) was opened. Then odor gas concentration within the flask was determined by means of Kitagawa typed detecting tube which had been connected to the rubber tube positioned at the end of the cock (b). The detector then started to suck up the malodor gas optionally present in the flask preceding to the opening of the cock (a).

(2) Test results

Methylmercaptan (ppm)

| | i) Methylmercaptan (ppm) | | | |
|---|---|---|---|---|
| Time | 0.5 hr | 2 hr | 4 hr | 6 hr |
| Blank figure | 45 | 42 | 40 | 37 |
| Example 1 | 13 | 5 | 1 | *ND |
| Example 2 | 13 | 6 | 1 | ND |
| Example 3 | 15 | 5 | 1 | ND |
| Example 4 | 3 | 0.8 | ND | ND |
| Example 5 | ND | ND | ND | ND |
| Example 6 | 25 | 12 | 7 | 1 |
| The gel sample prepared from Example 1 was allowed to stand at ambient temperature (25 to 30° C.) for a period of 6 months and the resultant aged product used for this test. | 15 | 6 | 1 | ND |

*ND means not detected

| Time | ii) Hydrogen sulfide (ppm) | | |
|---|---|---|---|
| | 0.5 hr | 1 hr | 2 hr |
| Blank figure | 500 | 500 | 460 |
| Example 1 | 10 | ND | ND |
| Example 2 | 10 | ND | ND |
| Example 3 | 9 | ND | ND |
| Example 4 | 4 | ND | ND |
| Example 5 | ND | ND | ND |
| Example 6 | 150 | 45 | Trace |
| The gel sample prepared from Example 1 was allowed to stand at ambient temperature (25 to 30° C.) for a period of 6 months and the resultant aged product used for this test. | 10 | ND | ND |

INDUSTRIAL UTILIZATION FIELD

From the results of a series of deodorization tests as mentioned above, it is clear that the gel-formed deodorant composition according to this invention is very effective for deodorization against acidic odor-generating substances such as hydrogen sulfide and methylmercaptan and further that even the gel product which had been allowed to stand at ambient temperature (25° to 30° C.) for a period of 6 months showed no reduction in deodorization activity, namely it had an excellent storage-stability. Accordingly, the gel-formed deodorant composition according to this invention can be utilized usefully to deodorize acidic malodors generating from sulfur-containing compounds , which are evolved in wide-spread fields ranging from the industrial world to standard households, and is stable for a prolonged period of time because of its solid gel form as well as very easy to handle including the time of exchanging the deodorizer for another.

I claim:

1. A deodorant composition in the form of gel containing chlorine dioxide, which comprises a gel product obtained by gelling an aqueous solution of stabilized chlorine dioxide with use of 1 to 25% by weight of a polyethylene-imine having a molecular weight of from 10,000 to 100,000 and 0.5 to 15% by weight of an epoxide crosslinking agent.

2. A deodorant composition according to claim 1 in which use is made of polyethylene-imine having a molecular weight of from 20,000 to 70,000, and the epoxide cross-linking agent is selected from the group consisting of ethylene glycol diglycidyl ether, polyethylene glycol diglycidyl ether, propylene glycol diglycidyl ether, polypropylene glycol diglycidyl ether, neopentyl glycol diglycidyl ether, trimethylolpropane polyglycidyl ether, polyglycerol polyglycidyl ether, glycerol polyglycidyl ether and diglycerol polyglycidyl ether.

* * * * *